United States Patent
Dorn et al.

(10) Patent No.: US 12,148,445 B2
(45) Date of Patent: Nov. 19, 2024

(54) EMOTION DETECTION AND MODERATION BASED ON VOICE INPUTS, ERRORS IN GAMEPLAY, PHYSIOLOGICAL INDICATORS OF HEART RATE OR SKIN TONE OF USERS OF A COMMUNICATION SESSION

(71) Applicant: Sony Interactive Entertainment Inc., Tokyo (JP)

(72) Inventors: Victoria Dorn, San Mateo, CA (US); Celeste Bean, San Mateo, CA (US); Olga Rudi, San Mateo, CA (US); Courtney Yingling, San Mateo, CA (US); Hsin-Yi Chien, San Mateo, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 17/491,269

(22) Filed: Sep. 30, 2021

(65) Prior Publication Data

US 2023/0096357 A1 Mar. 30, 2023

(51) Int. Cl.
*G10L 25/63* (2013.01)
*A61B 5/16* (2006.01)
(Continued)

(52) U.S. Cl.
CPC .............. *G10L 25/63* (2013.01); *G10L 15/22* (2013.01); *H04L 67/306* (2013.01); *H04N 7/152* (2013.01);
(Continued)

(58) Field of Classification Search
CPC ...... G10L 25/63; G10L 15/222; H04W 76/45; H04N 7/152; A61B 5/16
(Continued)

(56) References Cited

U.S. PATENT DOCUMENTS 10,293,260 B1 5/2019 Evans et al.
11,775,739 B2 10/2023 Yang et al.
(Continued)

FOREIGN PATENT DOCUMENTS

CN 102394919 A * 3/2012 ............... A61B 5/16
CN 118103835 5/2024
(Continued)

OTHER PUBLICATIONS

PCT Application No. PCT/US2022/034274 International Search Report and Written Opinion dated Sep. 28, 2022.
(Continued)

*Primary Examiner* — Farzad Kazeminezhad
(74) *Attorney, Agent, or Firm* — Polsinelli LLP (57) ABSTRACT

Systems and methods for emotion detection and emotion-based moderation based on voice inputs are provided. A user emotion profile may be stored in memory for a user. The user emotion profile may include one or more moderation rules that specifies a moderation action responsive to one or more emotional states. A current communication session associated with the user and one or more other users may be monitored based on the user emotion profile. An emotional state detected as being associated with a subset of the messages may trigger at least one of the moderation rules by corresponding to at least one of the emotional states specified by the user emotion profile. A presentation of at least one of the messages in the subset being provided to the user device may be modified in accordance with the moderation action specified by the user emotion profile.

19 Claims, 5 Drawing Sheets

(51) Int. Cl.
  *G10L 15/22* (2006.01)
  *H04L 67/306* (2022.01)
  *H04N 7/15* (2006.01)
  *H04W 76/45* (2018.01)

(52) U.S. Cl.
  CPC .............. *H04W 76/45* (2018.02); *A61B 5/16* (2013.01); *G10L 15/222* (2013.01)

(58) Field of Classification Search
  USPC ........................................................ 455/518
  See application file for complete search history.

(56) References Cited

U.S. PATENT DOCUMENTS

| | | |
|---|---|---|
| 2003/0033145 A1 | 2/2003 | Petrushin |
| 2004/0249634 A1 | 12/2004 | Degani et al. |
| 2006/0025214 A1 | 2/2006 | Smith |
| 2006/0079260 A1* | 4/2006 | Tillet .................. H04W 76/45 455/518 |
| 2006/0270918 A1 | 11/2006 | Stupp et al. |
| 2011/0083086 A1 | 4/2011 | Brownlow et al. |
| 2014/0223462 A1 | 8/2014 | Aimone et al. |
| 2014/0244264 A1 | 8/2014 | Thirumalainambi et al. |
| 2014/0270109 A1 | 9/2014 | Raihi et al. |
| 2017/0148343 A1 | 5/2017 | Merzenich et al. |
| 2018/0109482 A1 | 4/2018 | DeLuca et al. |
| 2019/0052471 A1 | 2/2019 | Panattoni et al. |
| 2019/0126152 A1 | 5/2019 | Taylor et al. |
| 2019/0325201 A1 | 10/2019 | Gujral et al. |
| 2020/0061477 A1 | 2/2020 | Mahlmeister et al. |
| 2020/0089767 A1 | 3/2020 | Ni et al. |
| 2020/0134298 A1 | 4/2020 | Zavesky et al. |
| 2020/0153772 A1 | 5/2020 | Bostick et al. |
| 2020/0164278 A1 | 5/2020 | Andre et al. |
| 2020/0175972 A1 | 6/2020 | Fan et al. |
| 2020/0197810 A1 | 6/2020 | Kung et al. |
| 2020/0298131 A1 | 9/2020 | Pinto et al. |
| 2021/0031106 A1 | 2/2021 | Alderman et al. |
| 2021/0076002 A1* | 3/2021 | Peters ..................... H04N 7/152 |
| 2021/0174805 A1* | 6/2021 | Wang ....................... G10L 25/63 |
| 2021/0185276 A1 | 6/2021 | Peters et al. |
| 2021/0272584 A1 | 9/2021 | McAlpine et al. |
| 2023/0125367 A1 | 4/2023 | Yang et al. |

FOREIGN PATENT DOCUMENTS

| | | | |
|---|---|---|---|
| WO | WO 2020/2140411 A1 * | 10/2022 | ............. G06F 16/03 |
| WO | WO 2023/055446 | 4/2023 | |
| WO | 2023075945 A1 | 5/2023 | |

OTHER PUBLICATIONS

U.S. Appl. No. 17/510,877 Non-Final Office Action dated Aug. 2, 2022.
PCT Application No. PCT/US2022/043571 International Search Report and Written Opinion dated Jan. 6, 2023.
U.S. Appl. No. 17/510,877 Final Office Action dated Jan. 11, 2023.
PCT Application No. PCT/US2022/034274 International Preliminary Report on Patentability mailed Apr. 11, 2024.
PCT Application No. PCT/US2022/043571, International Preliminary Report on Patentability dated May 10, 2024.

* cited by examiner

EMOTION DETECTION AND MODERATION BASED ON VOICE INPUTS, ERRORS IN GAMEPLAY, PHYSIOLOGICAL INDICATORS OF HEART RATE OR SKIN TONE OF USERS OF A COMMUNICATION SESSION

BACKGROUND OF THE INVENTION

1. Field of the Invention

The present invention generally relates to detection of emotions from system users. More specifically, the present invention relates to emotion detection and emotion-based moderation based on voice inputs.

2. Description of the Related Art

Presently available digital content titles may elicit different types of emotional responses in different users that interact with various digital elements in associated digital environments of such titles. Further, engagement with some digital content titles may involve interaction with other users within the digital (e.g., virtual) environment or within associated communication sessions. Such other users may exhibit their own emotions, and thus, the interaction with the other users may itself elicit or otherwise affect the types and extents of emotional states of users.

A user may wish to control the type of emotions that they encounter within an interactive (e.g., gameplay) session and within associated communication session(s). For example, a user may be stressed when other users are yelling or otherwise exhibiting anger. In such cases or in similar cases, the user's mental health or sensory processing conditions may deteriorate or otherwise suffer when exposed to others' negative emotions over extended periods of time. Another example may include players who may not wish to expose themselves to profanity, graphic content, bullying language, misgendering language, or other aggressive, hostile, or violent language (e.g., harassment, threats). In particular, young players (e.g., children) may have parents, guardians, or other supervisors (e.g., relatives, child-care professionals) who wish to limit their charge's exposure to such negative emotions and associated language.

There is, therefore, a need in the art for improved systems and methods of emotion detection and emotion-based moderation based on voice inputs.

SUMMARY OF THE CLAIMED INVENTION

Embodiments of the present invention include systems and methods for emotion detection and emotion-based moderation based on voice inputs. A user emotion profile may be stored in memory for a user. The user emotion profile may include one or more moderation rules that specifies a moderation action responsive to one or more emotional states. A current communication session associated with the user and one or more other users may be monitored based on the user emotion profile. An emotional state detected as being associated with a subset of the messages may trigger at least one of the moderation rules by corresponding to at least one of the emotional states specified by the user emotion profile. A presentation of at least one of the messages in the subset being provided to the user device may be modified in accordance with the moderation action specified by the user emotion profile.

DETAILED DESCRIPTION

Embodiments of the present invention include systems and methods for emotion detection and emotion-based moderation based on voice inputs. A user emotion profile may be stored in memory for a user. The user emotion profile may include one or more moderation rules that specifies a moderation action responsive to one or more emotional states. A current communication session associated with the user and one or more other users may be monitored based on the user emotion profile. An emotional state detected as being associated with a subset of the messages may trigger at least one of the moderation rules by corresponding to at least one of the emotional states specified by the user emotion profile. A presentation of at least one of the messages in the subset being provided to the user device may be modified in accordance with the moderation action specified by the user emotion profile.

Figure 1:
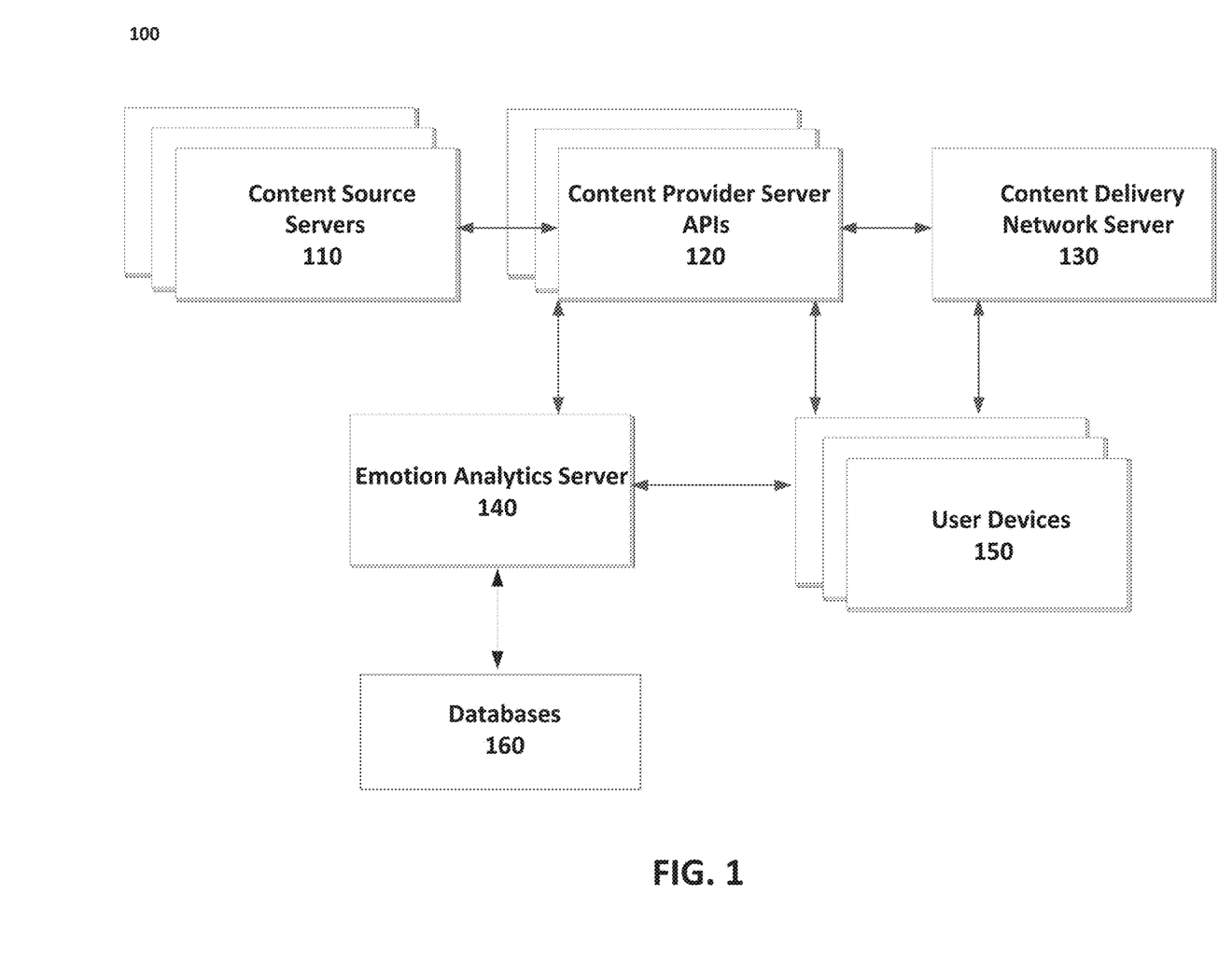
FIG. 1 illustrates a network environment in which a system for emotion detection and emotion-based moderation based on voice inputs may be implemented.

FIG. 1 illustrates a network environment in which a system for emotion detection and emotion-based moderation based on voice inputs may be implemented. The network environment 100 may include one or more content source servers 110 that provide digital content (e.g., games, other applications and services) for distribution, one or more content provider server application program interfaces (APIs) 120, content delivery network server 130, an emotion analytics server 140, and one or more user devices 150. The devices in network environment 100 communicate with each other using one or more communication networks, which may include a local, proprietary network (e.g., an intranet) and/or may be a part of a larger wide-area network. The communications networks may be a local area network (LAN), which may be communicatively coupled to a wide area network (WAN) such as the Internet. The Internet is a broad network of interconnected computers and servers allowing for the transmission and exchange of Internet Protocol (IP) data between users connected through a network service provider. Examples of network service providers are the public switched telephone network, a cable service provider, a provider of digital subscriber line (DSL) services, or a satellite service provider. One or more communications networks allow for communication between the various components of network environment 100.

The servers described herein may include any type of server as is known in the art, including standard hardware computing components such as network and media interfaces, non-transitory computer-readable storage (memory), and processors for executing instructions or accessing information that may be stored in memory. The functionalities of multiple servers may be integrated into a single server. Any of the aforementioned servers (or an integrated server) may take on certain client-side, cache, or proxy server characteristics. These characteristics may depend on the particular network placement of the server or certain configurations of the server.

Content source servers 110 may maintain and provide a variety of digital content and digital services available for distribution over a communication network. The content source servers 110 may be associated with any content provider that makes its content available for access over a communication network. The content source servers 110 may therefore host a variety of different content titles, which may further have be associated with object data regarding a digital or virtual object (e.g., activity information, zone information, character information, player information, other game media information, etc.) displayed in a digital or virtual environment during an interactive session.

Such content may include not only digital video and games, but also other types of digital applications and services. Such applications and services may include any variety of different digital content and functionalities that may be provided to user devices 150, including providing and supporting chat and other communication channels. The chat and communication services may be inclusive of voice-based, text-based, and video-based messages. Thus, a user device 150 may participate in a gameplay session concurrent with one or more communication sessions, and the gameplay and communication sessions may be hosted on one or more of the content source servers 110.

The content from content source server 110 may be provided through a content provider server API 120, which allows various types of content source servers 110 to communicate with other servers in the network environment 100 (e.g., user devices 150). The content provider server API 120 may be specific to the particular operating language, system, platform, protocols, etc., of the content source server 110 providing the content, as well as the user devices 150 and other devices of network environment 100. In a network environment 100 that includes multiple different types of content source servers 110, there may likewise be a corresponding number of content provider server APIs 120 that allow for various formatting, conversion, and other cross-device and cross-platform communication processes for providing content and other services to different user devices 150, which may each respectively use different operating systems, protocols, etc., to process such content. As such, applications and services in different formats may be made available so as to be compatible with a variety of different user device 150. In a network environment 100 that includes multiple different types of content source servers 110, content delivery network servers 130, emotion analytics server 140, user devices 150, and databases 160, there may likewise be a corresponding number of APIs managed by content provider server APIs 120.

The content provider server API 120 may further facilitate access of each of the user devices 150 to the content hosted or services provided by the content source servers 110, either directly or via content delivery network server 130. Additional information, such as metadata, about the accessed content or service can also be provided by the content provider server API 120 to the user device 150. As described below, the additional information (e.g., object data, metadata) can be usable to provide details about the content or service being provided to the user device 150. In some embodiments, the services provided from the content source servers 110 to the user device 150 via the content provider server API 120 may include supporting services that are associated with other content or services, such as chat services, ratings, and profiles that are associated with a particular game, team, community, etc. In such cases, the content source servers 110 may also communicate with each other via the content provider server API 120.

The content delivery network server 130 may include a server that provides resources, files, etc., related to the content from content source servers 110, including various content and service configurations, to user devices 150. The content delivery network server 130 can also be called upon by the user devices 150 that request to access specific content or services. Content delivery network server 130 may include universe management servers, game servers, streaming media servers, servers hosting downloadable content, and other content delivery servers known in the art.

Emotion analytics server 140 may include any data server known in the art that is capable of communicating with the different content source servers 110, content provider server APIs 120, content delivery network server 130, user devices 150, and databases 160. Such emotion analytics server 140 may be implemented on one or more cloud servers that carry out instructions associated with interactive content (e.g., games, activities, video, podcasts, User Generated Content ("UGC"), publisher content, etc.). The emotion analytics servers 140 may further carry out instructions, for example, for monitoring a communication session based on an emotion profile of a user, identifying and categorizing one or more emotional states associated with specific communications in the communication session in real-time, detecting when the emotional states trigger a moderation rule in the emotion profile, and modifying at least one message associated with the emotional state based on a moderation action of the emotion profile.

The user device 150 may include a plurality of different types of computing devices. The user device 150 may be a server that provides an internal service (e.g., to other servers) in network environment 100. In such cases, user device 150 may correspond to one of the content servers 110 described herein. Alternatively, the user device 150 may be a computing device that may include any number of different gaming consoles, mobile devices, laptops, and desktops. Such user devices 150 may also be configured to access data from other storage media, such as, but not limited to memory cards or disk drives as may be appropriate in the case of downloaded services. Such user devices 150 may include standard hardware computing components such as, but not limited to network and media interfaces, non-transitory computer-readable storage (memory), and processors for executing instructions that may be stored in memory. These user devices 150 may also run using a variety of different operating systems (e.g., iOS, Android), applications or computing languages (e.g., C++, JavaScript). An exemplary client device 150 is described in detail herein with respect to FIG. 5. Each user device 150 may be associated with participants (e.g., players) or other types (e.g., spectators) of users in relation to a collection of digital content streams.

While pictured separately, the databases 160 may be stored on any of the servers and devices illustrated in network environment 100 on the same server, on different servers, or on any of the user devices 150. Such databases 160 may store or link to various voice-emotion learning models, language-emotion models, or other emotion models, each of which may be specific to different emotions, users, or user groups. Databases 160 may also store other resources used for evaluating emotional states exhibited during communication sessions. In addition, databases 160 may store emotion profiles, as well as moderation rules that may be specific to and further customizable to a particular user, user group or team, user category, game title, game genre, language category, etc. One or more user emotion profiles may also be stored in the databases 160 for each user. In addition to gameplay data regarding the user (e.g., user progress in an activity and/or media content title, user ID, user game characters, etc.), the user emotion profile may include a set of triggers and moderation rules specific to the user.

Exemplary learning models associated with emotion identification may include a variety of detectable indicators, including textual indicators (e.g., diction or word choice, profanity, keywords, terms, phrases, etc.), verbal indicators (e.g., changes in voice intonation, pitch or frequency, rate or tempo of speech, rhythms, volume, etc.), visual indicators (e.g., facial expressions, skin tone (e.g., flushed or pale relative to calm states), physiological or behavioral indicators (e.g., biometric changes such as heart rate, signs of stress, increased errors in input, etc.), in-game indicators (e.g., errors in gameplay, character behaviors), and other indicators associated with mood, sentiment, emotion, etc., known in the art. The learning models may further be refined for different players, who may exhibit different indicators for a given emotion. A specific player may further be associated with multiple different learning models corresponding to different emotions. The learning models may further be refined based on user input from the user or from others who may provide feedback as to the emotional state of a particular user.

In addition to learning models associated with emotion, a user emotion profile may further include one or more moderation rules that are responsive to different emotional triggers. The moderation rules for the user may specify, for example, certain trigger conditions related to emotion and associated moderation actions. For example, a trigger condition may be include detecting indicators of undesired emotions (e.g., high volume, yelling, profanity, hate speech, racist, sexist, homophobic, mis-gendering language), and a corresponding moderation rule may specify reducing the volume, muting or replacing the objectionable language, and modulating the voice tone to be more neutral in relation to emotion (e.g., auto-tuning or otherwise changing a sound parameter of the original voice, using a voice generator to provide a new voice). When the moderation rules are applied to a communication session, therefore, a user may still participate in a communication session and comprehend the communications and messages that are exchanged, but may also avoid or neutralize undesired emotions. A user may therefore determine how to protect their own mental and emotional well-being and avoid stress related to such undesired emotions when interacting with other users in communication sessions. Such a user may also specify or customize moderation rules responsive to their own emotional states. Such moderation rules may concern decreasing game difficulty, level of aggressive gameplay, heightened thresholds for different emotional triggers, self-censorship of profanity, neutralizing or modifying one's own voice, triggering calming effects (e.g., music, visuals, fans and other temperature adjustments, etc.

In some embodiments, a user may specify a moderation rule that results in a visual display indicative of their own or other users' emotional states. Such a visual display may indicate different emotions and levels (e.g., low, medium, high) of such emotions. Different emotions may be visualized in an emotional dashboard, for example, that includes different types of measurement or metric presentation. Such visual displays may be triggered based on custom alert or notification settings as to thresholds associated with indicators for a certain emotion. In addition, the emotion analytics server 140 may also track data regarding emotional indicators over time, which may be used to develop and refine learning models associated with emotions. The user may also request to view the emotional dashboard (associated with their own emotional data or the emotional data of others), which may further breakdown the emotional data by game title, game session, interaction with different specific users or user groups, time periods, or any other parameter being tracked and made accessible to emotion analytics server 140 (including data tracked by UDS system 200).

In a communication session that involves multiple players each associated with different emotion profiles, therefore, each player may be presented with different versions of the same chat stream that has been moderated in accordance with their respective user emotion profiles. Thus, a chat stream that may include multiple different communications exhibiting different emotions in unmodified, unfiltered form may be transformed into different versions of the chat stream presented at each user device in accordance with their respective user emotion profiles. For example, one user—who may not have expressed any emotional triggers or moderation preferences or rules—may receive an original, unmodified version of the chat streams including messages as provided by each of the other users. Another user—who may have expressed preferences for avoiding profanity/hate speech—may therefore be presented with a different version of the chat stream from which all profanity and hate speech were removed or muted. Yet another user—who may have expressed a further preference for avoiding anger-laden communications—may be presented with yet a different version of the chat stream in which all anger-laden communications have been neutralized.

Such neutralization may be implemented by auto-tuning the specific communications into a more emotionally-neutral tone or by using a voice generator to generate a new tone. The new tone may correspond to a neutral, computer-generated voice or may correspond to preferred voices (e.g., cartoon character voices) associated with an opposite emotional effect. For example, a user may opt to change a voice detected as indicative of anger (or other negative emotion) to an auto-tuned or computer-generated cartoon voice associated with humor and comical effect. Such neutralization may also apply to textual language, for example, by replacing anger-laden words with replacements (e.g., language associated with neutral, humorous, comical effect, emojis, graphics, other user-generated content (UGC), etc.).

In some implementations, the user emotion profile may be set not only by the users themselves, but also parents, guardians, supervisors, etc., of the users who may wish their charge to avoid exposure to certain types of emotions and indicators of the same, including profanity, graphic content, bullying language, misgendering language, or other aggressive, hostile, or violent language (e.g., harassment, threats). Thus, the trigger conditions defined by the moderation rules may include various terms, phrases, and indicators of such language or content, while the associated moderation actions may include removing (e.g., deleting, muting, bleeping, auto-tuning, voice-generating) or modifying (e.g., blurring, blocking/blacking-out, auto-correcting or replacing with alternative language, emoji, graphics, UGC) the triggering language from the chat stream presentation provided to the user. For example, misgendering language or dead names may be replaced with the correct pronouns or chosen names associated with the user. As discussed herein, voices detected as being associated with an undesired emotion may also be modified by way of muting, modulating, auto-tuning, or replacement by a voice generator.

In some instances, a user may choose to censor themselves when customizing the moderation rules of their own user emotion profile. For example, the user may specify that certain audiences (e.g., players in young age ranges) be prevented from seeing, hearing, or accessing certain types of content generated by the user. As such, the trigger conditions may include parameters characterizing the other users and different ranges associated with different trigger actions. Female players may have different settings for modifying their own voices, for example, to allow or avoid indicators of their gender based on the identity or category of each of the other players in a communication session. Younger players may wish to modify their voices so as to appear older and more mature. In another example, the user may specify different categories of users (e.g., friends, teammates, current session players, favorites, trusted users, etc.) associated with different moderation rules as applied to their own voice or other voices. Thus, a chat stream may be further customized for the user based on application of the different moderation rules in the associated user emotion profile.

In some embodiments, the associated moderation action may include identifying a user who is the source of the triggering emotion (e.g., a specific player or spectator) and automatically adding the identified user to a block list or initiating another form of punishment or intervention (e.g., blocking access to gameplay session or platform, requiring remedial training as prerequisite to regaining gameplay privileges, in-game punishments affecting game status or gameplay). Some implementations of the trigger conditions may include a predetermined number of permitted uses (e.g., three strikes) before the identified user is blocked or other punishment or intervention imposed. As such, each detected use of triggering emotional indicators may be counted against the predetermined number and result in an update in the current status of the trigger condition (e.g., second strike out of three). Progressive punishments for repeat offenders may also be implemented locally or across the entire communication session, so that players who continue to exhibit the same undesirable behaviors may be subject to increasingly harsher or longer punishment.

Different combinations of the moderation rules (and associated trigger conditions and moderation actions) may be stored in the user emotion profile for each user. Collectively, therefore, the set of moderation rules included in a user emotion profile provides for custom evaluation, modification, and presentation for the specific user. The customization may further be based on current session conditions (e.g., current gameplay status, current game title, current in-game conditions). Because each chat stream presentation is personalized to the specific user based on their respective user emotion profile, a chat stream involving multiple different users may be modified to result in as many different versions of the chat stream as there are users. In some embodiments, emotion analytics server 140 may generate customized bots (including chatbots) programmed to apply a custom user emotion profile associated with a user to online communication sessions with which the user is participating via their respective user device. Such analysis and modification may therefore occur either at a remote emotion analytics server 140 or associated bot, locally via a bot or other application operated by the user device 150, or a combination.

In exemplary implementations, a current communication session involving multiple users may be monitored by emotion analytics server 140 in accordance with the respective user emotion profiles associated with each of the users. In monitoring for a particular user, the emotion analytics server 140 may detect in real-time that a subset of the messages (and parts of specific messages) of the current communication session triggers at least one of the moderation rules in the user emotion profile for that user. Such detection may be based on the message meeting one or more trigger conditions specified by the moderation rule. The emotion analytics server 140 may then moderate at least one message in real-time based on a moderation action specified by the triggered moderation rule. Such moderation action may result in modifying the at least one message that exhibits one or more of the trigger conditions. Further, emotion analytics server 140 may modify a presentation of the current communication session that is provided to the user device of the particular user. The presentation of the current communication session may be modified to remove or neutralize the trigger conditions.

Figure 2:
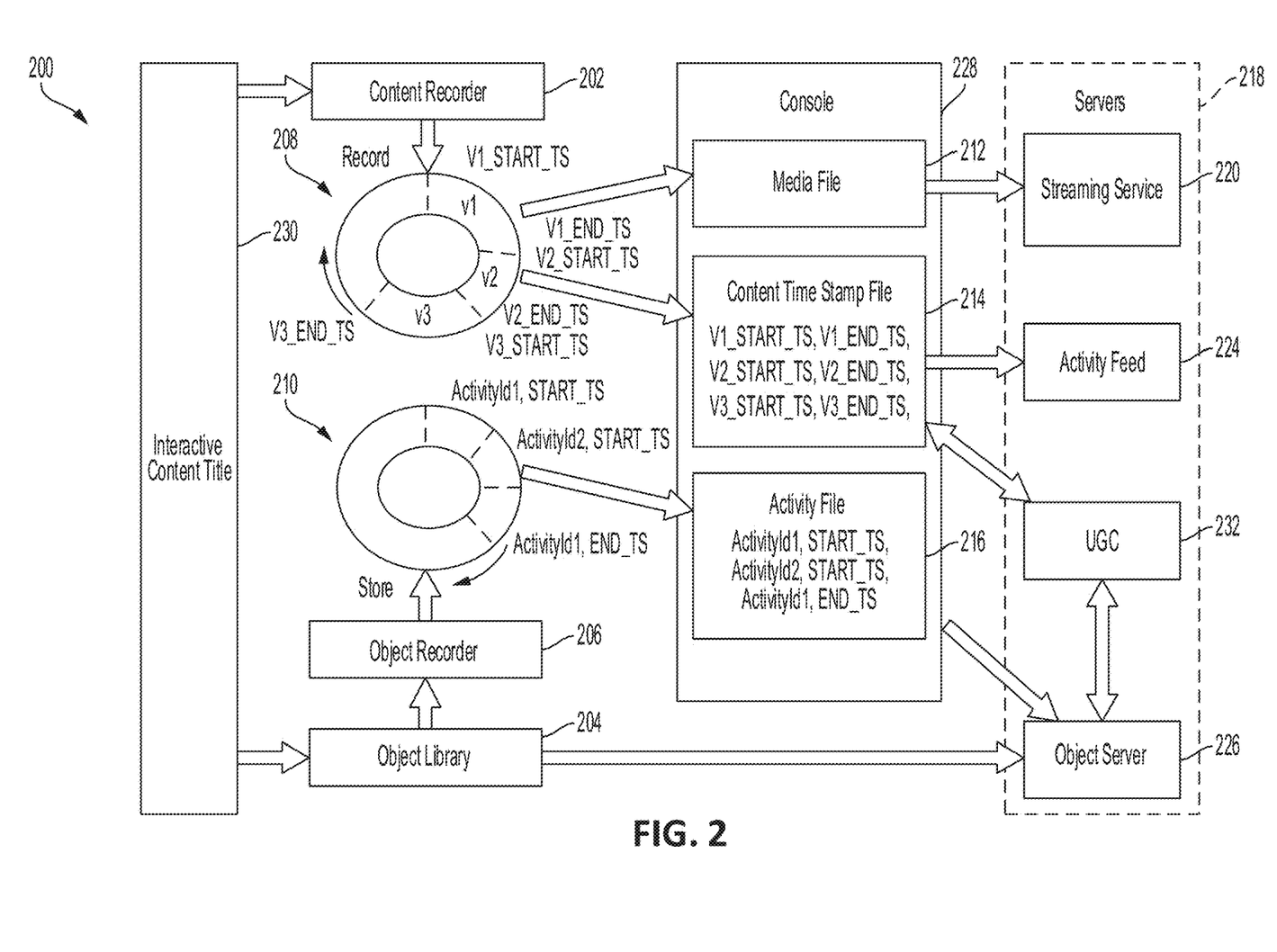
FIG. 2 illustrates an exemplary uniform data system (UDS) that may be used to provide data to a system for emotion detection and emotion-based moderation based on voice inputs.

During the course of a communication session, the user may also tag new emotional indicators for identification as an emotional trigger subject to moderation. Tagging may be based on a selection of textual language communications, transcripts of spoken language, recorded in-game behaviors (e.g., user-generated content as captured by UDS system 200), auto-generated menus of different indicators detected as being present in the current communication session, freeform descriptions, or other selection mechanisms known in the art. The tagged and newly identified emotional indicators may then be used to evaluate incoming communications within the current communication session. Further, the user emotional profile(s) may be updated in real-time, as well as used to update and refine the learning models associated with emotion analysis and identification.

FIG. 2 illustrates an exemplary uniform data system (UDS) 200 that may be used to provide data to a system for emotion detection and emotion-based moderation based on voice inputs. Based on data provided by UDS 200, emotion analytics server 140 can be made aware of the current session conditions, e.g., what in-game objects, entities, activities, and events that users and associated character(s) have engaged with, and thus support analysis of and coordination of emotion detection and emotion-based responses by emotion analytics server 140 with current gameplay and in-game activities. Each user interaction may be associated the metadata for the type of in-game interaction, location within the in-game environment, and point in time within an in-game timeline, as well as other players, objects, entities, etc., involved. Thus, metadata can be tracked for any of the variety of user interactions that can occur in during a game session, including associated activities, entities, settings, outcomes, actions, effects, locations, and character stats. Such data may further be aggregated, applied to data models, and subject to analytics. Such a UDS data model may be used to assign contextual information to each portion of information in a unified way across games.

For example, various content titles may depict one or more objects (e.g., involved in in-game activities) with which a user can interact and/or UGC (e.g., screen shots, videos, commentary, mashups, etc.) created by peers, publishers of the media content titles and/or third party publishers. Such UGC may include metadata by which to search for such UGC. Such UGC may also include information about the media and/or peer. Such peer information may be derived from data gathered during peer interaction with an object of an interactive content title (e.g., a video game, interactive book, etc.) and may be "bound" to and stored with the UGC. Such binding enhances UGC as the UGC may deep link (e.g., directly launch) to an object, may provide for information about an object and/or a peer of the UGC, and/or may allow a user to interact with the UGC.

As illustrated in FIG. 2, an exemplary console 228 (e.g., a user device 130) and exemplary servers 218 (e.g., streaming server 220, an activity feed server 224, an user-generated content (UGC) server 232, and an object server 226) are shown. In one example, the console 228 may be implemented on the platform server 120, a cloud server, or on any of the servers 218. In an exemplary example, a content recorder 202 may be implemented on the platform server 120, a cloud server, or on any of the servers 218. Such content recorder 202 receives and records content (e.g., media) from an interactive content title 230 onto a content ring-buffer 208. Such ring-buffer 208 may store multiple content segments (e.g., v1, v2 and v3), start times for each segment (e.g., V1_START_TS, V2_START_TS, V3_START_TS), and end times for each segment (e.g., V1_END_TS, V2_END_TS, V3_END_TS). Such segments may be stored as a media file 212 (e.g., MP4, WebM, etc.) by the console 228. Such media file 212 may be uploaded to the streaming server 220 for storage and subsequent streaming or use, though the media file 212 may be stored on any server, a cloud server, any console 228, or any user device 130. Such start times and end times for each segment may be stored as a content time stamp file 214 by the console 228. Such content time stamp file 214 may also include a streaming ID, which matches a streaming ID of the media file 212, thereby associating the content time stamp file 214 to the media file 212. Such content time stamp file 214 may be uploaded and stored to the activity feed server 224 and/or the UGC server 232, though the content time stamp file 214 may be stored on any server, a cloud server, any console 228, or any user device 130.

Concurrent to the content recorder 202 receiving and recording content from the interactive content title 230, an object library 204 receives data from the interactive content title 230, and an object recorder 206 tracks the data to determine when an object beings and ends. The object library 204 and the object recorder 206 may be implemented on the platform server 120, a cloud server, or on any of the servers 218. When the object recorder 206 detects an object beginning, the object recorder 206 receives object data (e.g., if the object were an activity, user interaction with the activity, activity ID, activity start times, activity end times, activity results, activity types, etc.) from the object library 204 and records the activity data onto an object ring-buffer 210 (e.g., ActivityID1, START_TS; ActivityID2, START_TS; ActivityID3, START_TS). Such activity data recorded onto the object ring-buffer 210 may be stored in the object file 216. Such object file 216 may also include activity start times, activity end times, an activity ID, activity results, activity types (e.g., competitive match, quest, task, etc.), user or peer data related to the activity. For example, an object file 216 may store data regarding an item used during the activity. Such object file 216 may be stored on the object server 226, though the object file 216 may be stored on any server, a cloud server, any console 228, or any user device 130.

Such object data (e.g., the object file 216) may be associated with the content data (e.g., the media file 212 and/or the content time stamp file 214). In one example, the UGC server 232 stores and associates the content time stamp file 214 with the object file 216 based on a match between the streaming ID of the content time stamp file 214 and a corresponding activity ID of the object file 216. In another example, the object server 226 may store the object file 216 and may receive a query from the UGC server 232 for an object file 216. Such query may be executed by searching for an activity ID of an object file 216 that matches a streaming ID of a content time stamp file 214 transmitted with the query. In yet another example, a query of stored content time stamp files 214 may be executed by matching a start time and end time of a content time stamp file 214 with a start time and end time of a corresponding object file 216 transmitted with the query. Such object file 216 may also be associated with the matched content time stamp file 214 by the UGC server 232, though the association may be performed by any server, a cloud server, any console 228, or any user device 130. In another example, an object file 216 and a content time stamp file 214 may be associated by the console 228 during creation of each file 216, 214.

In exemplary embodiments, the media files 212 and activity files 216 may provide information to emotion analytics server 140 regarding current session conditions. Emotion analytics server 140 may therefore use such media files 212 and activity files 216 to determine whether the current session conditions meet any of the trigger conditions of the moderation rules associated with the current users of a monitored communication session. For example, the media files 212 and activity files 216 may include references to particular characters, locations, and objects displayed and interacted with in a current gameplay session. Based on such files 212 and 216, therefore, emotion analytics server 140 may identify in-game behaviors may be indicative of emotion rather than competitive gameplay. For example, unusual behaviors such as attacking a teammate while yelling profanities may be identified as being indicators of anger rather than a good faith effort to compete within the context of the game session. As such, evaluation of whether current in-game data meets a trigger conditions may include evaluation of certain in-game status of the user or other users. In such cases, the emotion analytics server 140 may use media files 212 and activity files 216 to evaluate and determine whether such in-game status meets or contributes to the trigger conditions.

Figure 3:
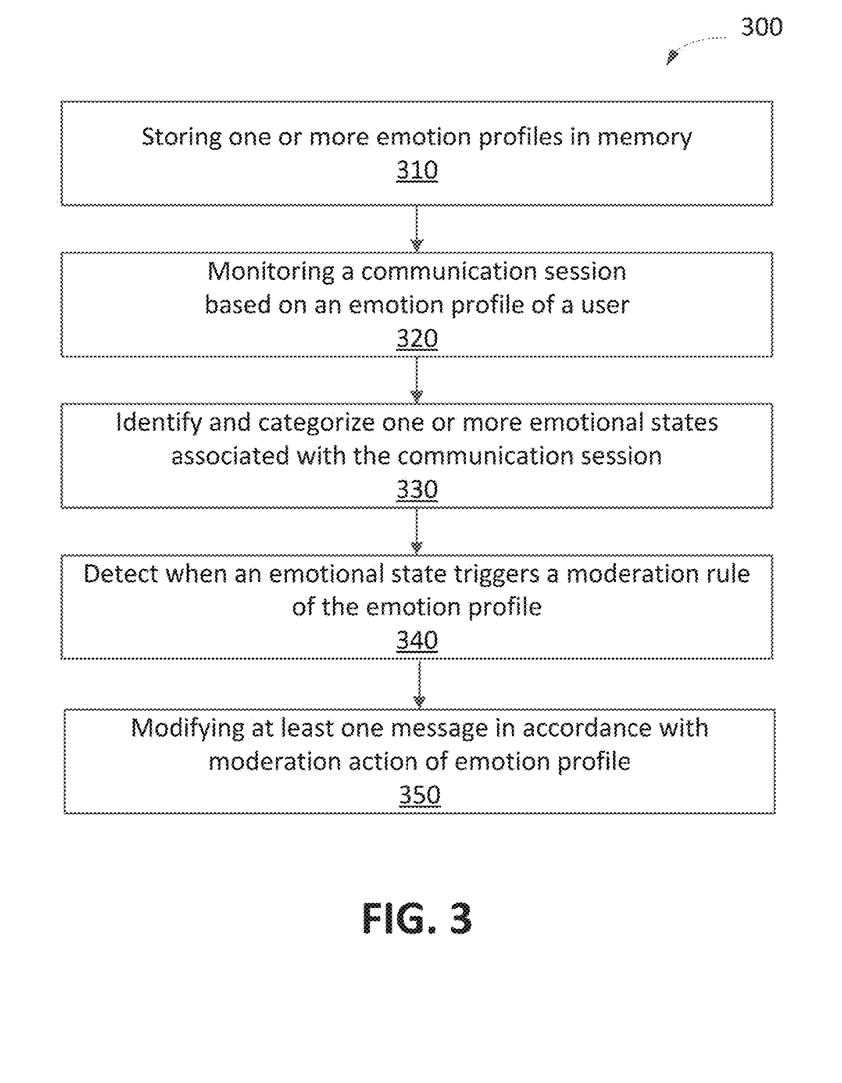
FIG. 3 is a flowchart illustrating an exemplary method for emotion detection and emotion-based moderation based on voice inputs.

FIG. 3 is a flowchart illustrating an exemplary method 300 for emotion detection and emotion-based moderation based on voice inputs. The method 300 of FIG. 3 may be embodied as executable instructions in a non-transitory computer readable storage medium including but not limited to a CD, DVD, or non-volatile memory such as a hard drive. The instructions of the storage medium may be executed by a processor (or processors) to cause various hardware components of a computing device hosting or otherwise accessing the storage medium to effectuate the method. The steps identified in FIG. 3 (and the order thereof) are exemplary and may include various alternatives, equivalents, or derivations thereof including but not limited to the order of execution of the same.

In step 310, a user emotion profile may be stored in memory (e.g., databases 160) for a particular user. Different users may be associated different user emotion profiles, as each user emotion profile may be customized to the preferences, habits, and histories of the respective user. Each user emotion profile may include one or more moderation rules, each of which may specify one or more triggering emotional conditions associated with one or more moderation actions. The triggering emotional conditions may pertain to any emotional condition regarding the user, other users, the messages in a given communication session, and associated content session(s). Meanwhile, the moderation actions may include muting, modifying, or replacing verbal and/or textual language from the communication session, presentation modification, and other modifications to the chat stream.

In step 320, a current communication session may be monitored by emotion analytics server 140 based on the user emotion profiles of the participating users. As each user has their own respective user emotion profile, emotion analytics server 140 may retrieve the associated user emotion profiles from databases 160 and use the associated moderation rules to monitor a communication session in real-time (or close to real-time). Further, where the associated moderation rules may specify trigger conditions involving other or associated sessions (e.g., gameplay sessions), the emotion analytics server 140 may also obtain media files 212 and activity files 216 associated with the user who specified such trigger conditions. The media files 216 and activity files 216 may be used by emotion analytics server 140 in conjunction with the conditions of the communication session to determine whether the trigger conditions are met.

In step 330, a set of indicators associated with one or more messages in the communication session may be detected as triggering a moderation rule associated with a user. As noted above, the set of indicators may trigger the moderation rule when the trigger conditions specified by that moderation rule are met by the indicators. Because different users may be associated with different moderation rules via their respective different user emotion profiles, a set of indicators that triggers a moderation rule for one user may not trigger any moderation rule for another user. In a multiuser communication session where all users have different emotion profiles, different messages may trigger different levels and types of moderation for each different user.

In step 340, the emotion analytics server 140 may modify the message detected in step 330 by modifying (e.g., filtering, removing, etc.) the trigger conditions in accordance with the moderation actions of the triggered moderation rule. As noted above, such modifications may include adding to, removing, or otherwise changing the trigger conditions exhibited by the message. In some implementations, such modifications may result in filtering the message in part or entirely out of the chat stream of the communication session.

In step 350, the emotion analytics server 140 may modify the presentation of the current communication session provided to the user device 150 in accordance with the moderation actions of the triggered moderation rule. The presentation modification may include changing the content (e.g., specific words, terms, phrases) of triggering communications that is presented to the user device 150, as well as changing how such content is presented to the user device 150. Further, different media elements (e.g., from media files 216, activity files 216, or predefined media specified by moderation rules) may be added to or removed from the chat stream before being presented to the specific user associated with the triggered moderation rule.

Figure 4:
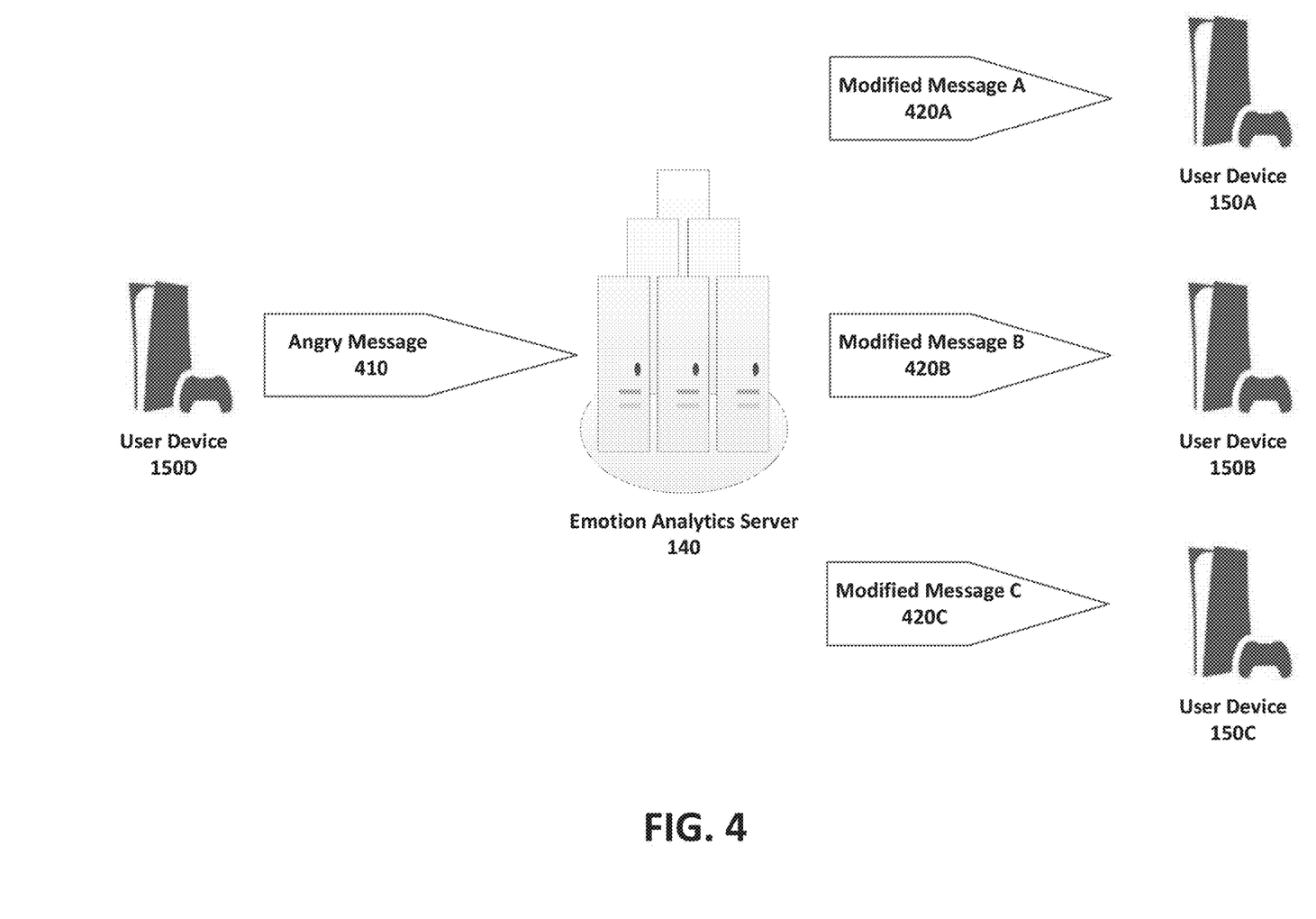
FIG. 4 is a diagram illustrating an exemplary implementation of emotion detection and emotion-based moderation based on voice inputs.

FIG. 4 is a diagram illustrating an exemplary implementation of emotion detection and emotion-based moderation based on voice inputs. The diagram of FIG. 4 illustrates user devices 150A-D that may be part of the same communication session being monitored by emotion analytics server 140. Where the communication session may be associated with a gameplay session, emotion analytics server 140 may further monitor the gameplay session or otherwise obtain data regarding the gameplay session (e.g., via UDS system 200).

As discussed above, each user of user devices 150A-D may be associated with their own respective user emotion profile(s). The emotion analytics server 140 may therefore monitor all communications originating from user devices 150A-D and evaluate whether such communications meet the triggering emotion conditions in the user emotion profiles of the users participating in the communication session. Where triggering emotion conditions are detected, the associated moderation rule(s) may be applied to the message or messages exhibiting or associated with the triggering emotion condition.

In an exemplary implementation, the user of user device 150D may originate a message identified as being associated with anger (e.g., angry message 410. The emotion analytics server 140 may identify indicators of anger in real-time as being present in or exhibited by angry message 410, which may include a text-based chat message or verbal chat message (including in-video speech). Such indicators may be associated with the angry message 410 itself or may be associated with the context within which the angry message 410 appeared. For example, the angry message 410 may have appeared at the same time that the user of user device 150D suffered an in-game loss or setback. Depending on the emotion profiles of each of the user devices 150A-D (including the originator of the angry message 410), the presentation of the angry message 410 may be modified in real-time to result in different modified messages 420A-C sent to user devices 150A-C. Thus, the user devices 150A-C may present different versions of the messages in communication session in real-time based on the respective emotion profiles.

For example, the emotion profile associated with the user of user device 150D—who originated the angry message 410—may include moderation rules applicable to their own messages, which may be used for self-censorship or otherwise automatically guarding against exposure of certain information (e.g., indicators of age, gender). In such instances, the same moderation rule may be applied to modify an aspect of the angry message 410 within each of the modified messages 420A-C provided to user devices 150A-C. For example, the emotion profile associated with the user of user device 150D may specify that all outgoing voice-based messages from user device 150D be modified in accordance with a moderation action that results in a computer-generated voice and vocal effects corresponding to a favorite game character.

In addition, the emotion profiles associated with the users of user devices 150A-C may further specify different moderation rules applicable to incoming messages. For example, the emotion profile associated with the user of user device 150A may not specify any moderation rules that are triggered by angry message 410, but may nevertheless be presented with modified message 420A based on the moderation rules of the user of user device 410D who originated the angry message, i.e., the angry message 410 as voiced by the favorite game character of the user of user device 410D.

Meanwhile, the emotion profile associated with the user of user device 150B may specify a triggering emotional condition as being met by profanity and that a corresponding moderation action mute the any profanity. Applying such a moderation action to the angry message 410 may include identifying specific words or phrases that constitute profanity within the angry message 410 and muting the identified words or phrases to generate modified message 420B that is then provided to user device 150B.

At the same time, the emotion profile associated with the user of user device 150C may specify a triggering emotional condition as being met by voice-based indicators of anger and that a corresponding moderation action modulate or modify the voice to remove the voice-based indicators of anger. Applying such a moderation action to the angry message 410 may include identifying specific voice-based words or phrases that exhibit the indicators of anger within the angry message 410 and auto-tuning the identified words or phrases in the angry message 410 to remove such indicators of anger (or using a computer-based voice generator to recreate the content of angry message 410 without the voice-based indicators of anger). As such, modified message 420A may be generated and then provided to user device 150A.

Figure 5:
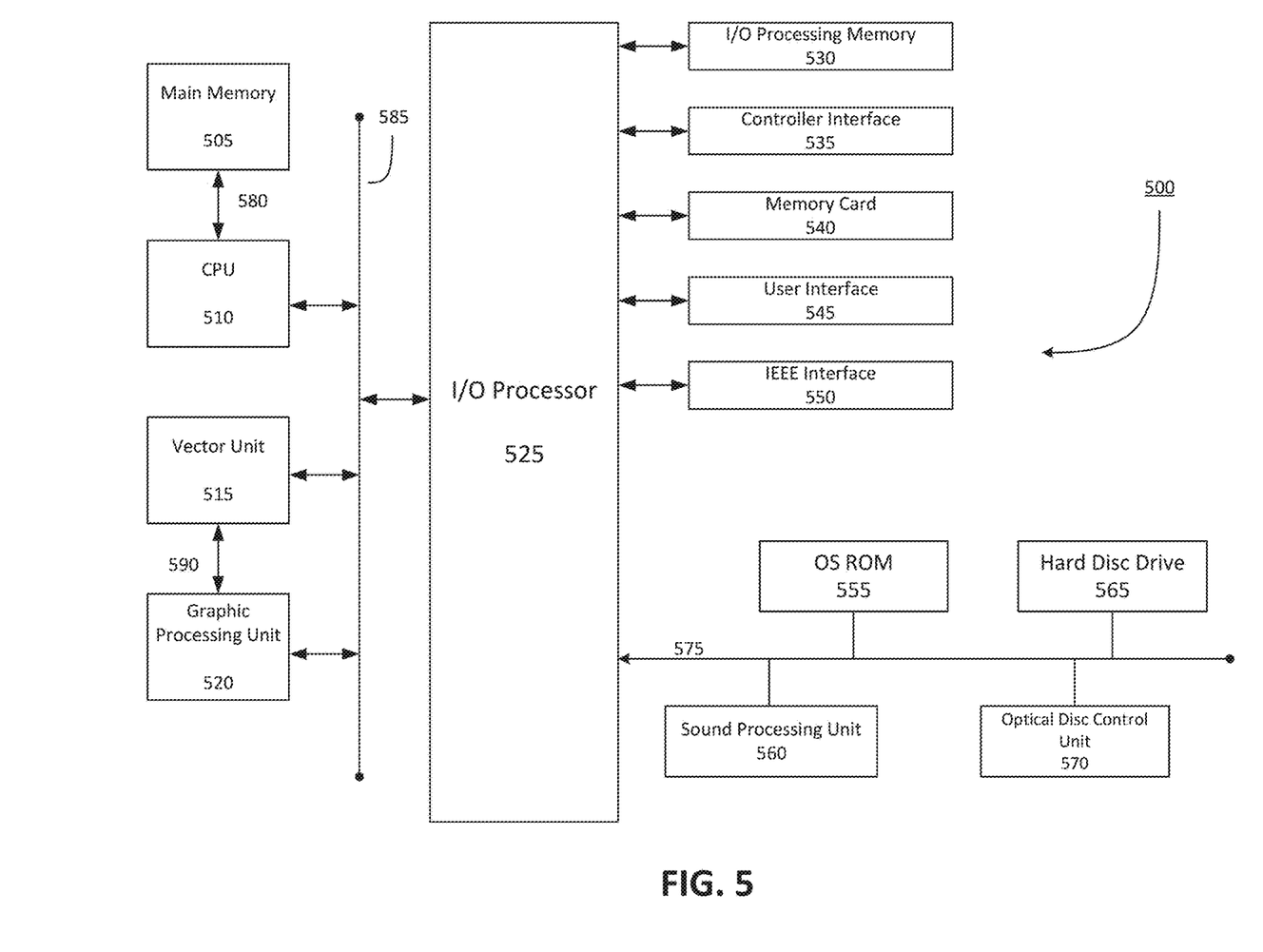
FIG. 5 is a block diagram of an exemplary electronic entertainment system that may be used in embodiments of the present invention.

FIG. 5 is a block diagram of an exemplary electronic entertainment system that may be used in embodiments of the present invention. The entertainment system 500 of FIG. 5 includes a main memory 505, a central processing unit (CPU) 510, vector unit 515, a graphics processing unit 520, an input/output (I/O) processor 525, an I/O processor memory 530, a controller interface 535, a memory card 540, a Universal Serial Bus (USB) interface 545, and an IEEE interface 550. The entertainment system 500 further includes an operating system read-only memory (OS ROM) 555, a sound processing unit 560, an optical disc control unit 570, and a hard disc drive 565, which are connected via a bus 575 to the I/O processor 525.

Entertainment system 500 may be an electronic game console. Alternatively, the entertainment system 500 may be implemented as a general-purpose computer, a set-top box, a hand-held game device, a tablet computing device, or a mobile computing device or phone. Entertainment systems may contain more or less operating components depending on a particular form factor, purpose, or design.

The CPU 510, the vector unit 515, the graphics processing unit 520, and the I/O processor 525 of FIG. 5 communicate via a system bus 585. Further, the CPU 510 of FIG. 5 communicates with the main memory 505 via a dedicated bus 580, while the vector unit 515 and the graphics processing unit 520 may communicate through a dedicated bus 590. The CPU 510 of FIG. 5 executes programs stored in the OS ROM 555 and the main memory 505. The main memory 505 of FIG. 5 may contain pre-stored programs and programs transferred through the I/O Processor 525 from a CD-ROM, DVD-ROM, or other optical disc (not shown) using the optical disc control unit 570. I/O Processor 525 of FIG. 5 may also allow for the introduction of content transferred over a wireless or other communications network (e.g., 4$, LTE, 3G, and so forth). The I/O processor 525 of FIG. 5 primarily controls data exchanges between the various devices of the entertainment system 500 including the CPU 510, the vector unit 515, the graphics processing unit 520, and the controller interface 535.

The graphics processing unit 520 of FIG. 5 executes graphics instructions received from the CPU 510 and the vector unit 515 to produce images for display on a display device (not shown). For example, the vector unit 515 of FIG. 5 may transform objects from three-dimensional coordinates to two-dimensional coordinates, and send the two-dimensional coordinates to the graphics processing unit 520. Furthermore, the sound processing unit 560 executes instructions to produce sound signals that are outputted to an audio device such as speakers (not shown). Other devices may be connected to the entertainment system 500 via the USB interface 545, and the IEEE 1394 interface 550 such as wireless transceivers, which may also be embedded in the system 500 or as a part of some other component such as a processor.

A user of the entertainment system 500 of FIG. 5 provides instructions via the controller interface 535 to the CPU 510. For example, the user may instruct the CPU 510 to store certain game information on the memory card 540 or other non-transitory computer-readable storage media or instruct a character in a game to perform some specified action.

The present invention may be implemented in an application that may be operable by a variety of end user devices. For example, an end user device may be a personal computer, a home entertainment system (e.g., Sony PlayStation2® or Sony PlayStation3® or Sony PlayStation4®), a portable gaming device (e.g., Sony PSP® or Sony Vita®), or a home entertainment system of a different albeit inferior manufacturer. The present methodologies described herein are fully intended to be operable on a variety of devices. The present invention may also be implemented with cross-title neutrality wherein an embodiment of the present system may be utilized across a variety of titles from various publishers.

The present invention may be implemented in an application that may be operable using a variety of devices. Non-transitory computer-readable storage media refer to any medium or media that participate in providing instructions to a central processing unit (CPU) for execution. Such media can take many forms, including, but not limited to, non-volatile and volatile media such as optical or magnetic disks and dynamic memory, respectively. Common forms of non-transitory computer-readable media include, for example, a floppy disk, a flexible disk, a hard disk, magnetic tape, any other magnetic medium, a CD-ROM disk, digital video disk (DVD), any other optical medium, RAM, PROM, EPROM, a FLASHEPROM, and any other memory chip or cartridge.

Various forms of transmission media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU. Various forms of storage may likewise be implemented as well as the necessary network interfaces and network topologies to implement the same.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A method for emotion-based moderation, the method comprising:
storing a user emotion profile in memory for a user, wherein the user emotion profile includes one or more moderation rules that specify a moderation action responsive to one or more emotional states of other users;
monitoring a current communication session associated with a user device of the user based on the user emotion profile, wherein the current communication session includes messages from one or more other user devices of the other users;
identifying an emotional state of one of the other users based on analyzing a subset of the messages from the other user using an emotion learning model that correlates emotion to one or more emotional indicators including at least one of error in gameplay, character behavior, or player physiological indicator that includes at least one of a heart rate or a skin tone;

detecting that the emotional state identified for the other user triggers at least one of the moderation rules, wherein the detected emotional state corresponds to at least one of the emotional states specified by the user emotion profile; and modifying a presentation of at least one of the messages in the subset being provided to the user device in accordance with the at least one triggered moderation rule, wherein at least a part of the at least one message is filtered out of the modified presentation in accordance with the moderation action specified by the at least one triggered moderation rule from the user emotion profile of the user, and wherein the modified presentation is different from a version provided to each of the other users of the current communication session.

2. The method of claim 1, wherein monitoring the current communication session includes monitoring emotional states associated with the user and with each of the other users.

3. The method of claim 2, wherein monitoring the current communication session further includes assigning the emotional states associated with the user and with each of the other users to one or more predetermined categories.

4. The method of claim 3, wherein the predetermined categories include one or more subcategories corresponding to a gradient between mild and extreme levels of the associated emotional state.

5. The method of claim 1, wherein the subset of messages is associated with one or more identified users within the current communication session.

6. The method of claim 5, further comprising imposing a punishment for the identified users, wherein the punishment includes a loss of one or more privileges associated with the current communication session.

7. The method of claim 1, wherein modifying the presentation of the at least one message includes neutralizing the detected emotional state associated with the at least one message.

8. A system for emotion-based moderation, the system comprising:

memory that stores a user emotion profile for a user, wherein the user emotion profile includes one or more moderation rules that specify a moderation action responsive to one or more emotional states of other users;

a communication interface that communicates over a communication network, wherein the communication interface connects to a current communication session associated with a user device of the user, wherein the current communication session includes messages from one or more other user devices of the other users; and a processor that executes instructions stored in memory, wherein the processor executes the instructions to:

monitor the current communication session based on the user emotion profile, identify an emotional state of one of the other users based on analyzing a subset of the messages from the other user using an emotion learning model that correlates emotion to one or more emotional indicators including at least one of error in gameplay, character behavior, or player physiological indicator that includes at least one of a heart rate or a skin tone;

detect that the emotional state identified for the other user triggers at least one of the moderation rules, wherein the detected emotional state corresponds to at least one of the emotional states specified by the user emotion profile, and modify a presentation of at least one of the messages in the subset being provided to the user device in accordance with the at least one triggered moderation rule, wherein at least a part of the at least one message is filtered out of the modified presentation in accordance with the moderation action specified by the at least one triggered moderation rule from the user emotion profile of the user, and wherein the modified presentation is different from a version provided to each of the other users of the current communication session.

9. The system of claim 8, wherein the processor monitors the current communication session by monitoring emotional states associated with the user and with each of the other users.

10. The system of claim 9, wherein the processor monitors the current communication session by further assigning the emotional states associated with the user and with each of the other users to one or more predetermined categories.

11. The system of claim 10, wherein the predetermined categories include one or more subcategories corresponding to a gradient between mild and extreme levels of the associated emotional state.

12. The system of claim 8, wherein the subset of messages is associated with one or more identified users within the current communication session.

13. The system of claim 12, wherein the processor executes further instructions to impose a punishment for the identified users, wherein the punishment includes a loss of one or more privileges associated with the current communication session.

14. The system of claim 8, wherein the processor modifies the presentation of the at least one message by neutralizing the detected emotional state associated with the at least one message.

15. A non-transitory, computer-readable storage medium, having embodied thereon a program executable by a processor to perform a method for emotion-based moderation, the method comprising:

storing a user emotion profile in memory for a user, wherein the user emotion profile includes one or more moderation rules that specify a moderation action responsive to one or more emotional states of other users;

monitoring a current communication session associated with a user device of the user based on the user emotion profile, wherein the current communication session includes messages from one or more other user devices of the other users;

identifying an emotional state of one of the other users based on analyzing a subset of the messages from the other user using an emotion learning model that correlates emotion to one or more emotional indicators including at least one of error in gameplay, character behavior, or player physiological indicator that includes at least one of a heart rate or a skin tone;

detecting that the emotional state identified for the other user triggers at least one of the moderation rules, wherein the detected emotional state corresponds to at least one of the emotional states specified by the user emotion profile; and modifying a presentation of at least one of the messages in the subset being provided to the user device in accordance with the at least one triggered moderation rule, wherein at least a part of the at least one message is filtered out of the modified presentation in accordance with the moderation action specified by the at least one triggered moderation rule from the user emotion profile of the user, and wherein the modified presentation is different from a version provided to each of the other users of the current communication session.

16. The non-transitory, computer-readable storage medium of claim 15, wherein monitoring the current communication session further includes assigning the emotional states associated with the user and with each of the other users to one or more predetermined categories.

17. The non-transitory, computer-readable storage medium of claim 16, wherein the predetermined categories include one or more subcategories corresponding to a gradient between mild and extreme levels of the associated emotional state.

18. The non-transitory, computer-readable storage medium of claim 15, wherein the subset of messages is associated with one or more identified users within the current communication session.

19. The non-transitory, computer-readable storage medium of claim 15, further comprising instructions executable to impose a punishment for the identified users, wherein the punishment includes a loss of one or more privileges associated with the current communication session.

* * * * *